(12) United States Patent
Nishiyama et al.

(10) Patent No.: US 8,466,287 B2
(45) Date of Patent: Jun. 18, 2013

(54) PROCESS FOR PRODUCING TRICYCLIC KETONE

(75) Inventors: Hiroyuki Nishiyama, Tokyo (JP); Seigo Sawada, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/278,579

(22) Filed: Oct. 21, 2011

(65) Prior Publication Data

US 2012/0041204 A1 Feb. 16, 2012

Related U.S. Application Data

(62) Division of application No. 11/921,776, filed as application No. PCT/JP2006/314482 on Jun. 8, 2006, now Pat. No. 8,067,595.

(30) Foreign Application Priority Data

Jun. 9, 2005 (JP) .................................. 2005-169346

(51) Int. Cl.
*C07D 491/147* (2006.01)
*C07D 491/22* (2006.01)
*C07C 223/02* (2006.01)

(52) U.S. Cl.
USPC ................................ 546/89; 564/502; 546/48

(58) Field of Classification Search
USPC ....................... 564/502; 546/89, 48
See application file for complete search history.

(56) References Cited

U.S. PATENT DOCUMENTS

| 3,687,954 | A | * | 8/1972 | Tyler et al. | .................... 544/382 |
| 3,957,764 | A | | 5/1976 | Lund | |
| 5,491,237 | A | | 2/1996 | Fang et al. | |
| 5,837,673 | A | | 11/1998 | Tsujihara et al. | |
| 7,126,000 | B2 | | 10/2006 | Ogawa et al. | |

| 2004/0106830 | A1 | 6/2004 | Ogawa et al. |
| 2004/0266803 | A1 | 12/2004 | Wani et al. |
| 2008/0103309 | A1 | 5/2008 | Laitinen |

FOREIGN PATENT DOCUMENTS

| JP | 51-8955 B | 3/1976 |
| JP | 07-101956 A | 4/1995 |
| JP | 09-512559 A | 12/1997 |
| JP | 10-072467 A | 3/1998 |
| JP | 11-279104 A | 10/1999 |
| JP | 2004-514786 A | 5/2004 |
| JP | 2008-529993 A | 8/2008 |
| WO | WO 96/31513 A1 | 10/1996 |
| WO | WO 01/49291 A1 | 7/2001 |
| WO | WO 02/42249 A1 | 5/2002 |
| WO | WO 02/066416 A1 | 8/2002 |
| WO | WO 2004/073601 A2 | 9/2004 |

OTHER PUBLICATIONS

European Office Action issued Aug. 2, 2012 in connection with European Application No. 06757154.7.
Olah et al., Formylating Agents. Chem Rev. Aug. 1987;87(4):671-86.
Imura et al., Enantioselective synthesis of 20(S)-camptothecin using an enzyme-catalyzed resolution. Tetrahedron: Asymmetry. Jul. 1998;9(13):2285-2291.
Jew et al., Enantioselective Synthesis of 20(S)-Camptothecin Using Sharpless Catalytic Asymmetric Dihydroxylation. Tetrahedron: Asymmetry. Jun. 1995; 6(6):1245-8.
Finkelstein, M. et al., "Anodic Oxidation of N-Methylformamide and N-Methylacetamide," *Tetrahedron* 1972; 28:4497-4502.
Ross, S.R. et al., "Reactions of N-Formyloxymethyl-N-methylformamide. A useful electrophilic reagent," *The Journal of Organic Chemistry* 1966; 31(1):133-137.

* cited by examiner

*Primary Examiner* — Charanjit Aulakh
(74) *Attorney, Agent, or Firm* — Wolf, Greenfield & Sacks, P.C.

(57) ABSTRACT

In order to efficiently supply CPT, which is a starting compound of irinotecan hydrochloride and a variety of camptothecin derivatives, by a practical total synthesis, the invention provides a means of efficiently preparing a tricyclic ketone that corresponds to a CDE ring moiety of a camptothecin (CPT) skeleton.

15 Claims, No Drawings

PROCESS FOR PRODUCING TRICYCLIC KETONE

RELATED APPLICATIONS

This application is a divisional application of U.S. application Ser. No. 11/921,776 filed Jul. 15, 2008, now U.S. Pat. No. 8,067,595, which is a national stage application under 35 U.S.C. §371 of PCT International application PCT/JP2006/311482, filed Jun. 8, 2006. The entire text of each of the above-referenced disclosures is specifically incorporated herein by reference without disclaimer.

TECHNICAL FIELD

The present invention relates to a process for preparing an intermediate involved in the synthesis of camptothecins having antitumor activity and to a novel formylation reagent used in the preparation process. More particularly, it relates to an asymmetric synthetic method for a compound that is a starting material in preparing various types of camptothecin derivatives and has a tricyclic ketone moiety corresponding to the CDE ring moiety in the skeleton of camptothecins.

BACKGROUND ART

Camptothecin (hereinafter, referred to as CPT) isolated from the bark, root, fruit, leaf and the like of *Camptotheca acuminata*, which is native to China, is a pentacyclic alkaloid, and is known to exhibit antitumor activity by inhibiting nucleic acid synthesis. On the other hand, it has been reported that camptothecin derivatives induce side effects such as diarrhea ('Gan to Kagakuryoho' (Cancer & Chemotherapy) 17, p 115-120, 1990) and disorders of the digestive organs; because of these situations, various types of derivatives have been studied with the object of reducing the toxicity, increasing the effect, etc.

The present inventors have already reported, as a compound having suppressed toxicity compared with CPT, 7-ethyl-10-[4-(1-piperidino)-1-piperidino]carbonyloxy-camptothecin hydrochloride trihydrate (hereinafter, referred to as CPT-11), which is a water-soluble semisynthetic derivative of CPT and is currently widely used as an antitumor agent (generic name; irinotecan hydrochloride).

Camptothecins such as CPT-11 may be obtained by chemical modification of CPT obtained from natural materials.

However, since the amount of CPT obtained from a natural material such as *Camptotheca acuminata*, which is a raw material, is extremely small, it is anticipated that it will become difficult to supply a sufficient amount of CPT because of a highly increased demand of CPT-11. Furthermore, preparation methods by total synthesis have been studied, but it is not practical at present.

The present inventors have synthesized 4-iodo-2-methoxy-6-trimethylsilylpyridine-3-carbaldehyde (hereinafter, referred to as compound (b)), which is an intermediate in the synthesis of a tricyclic ketone moiety corresponding to the CDE ring moiety of CPTs, by the scheme below (Patent Publication 1),

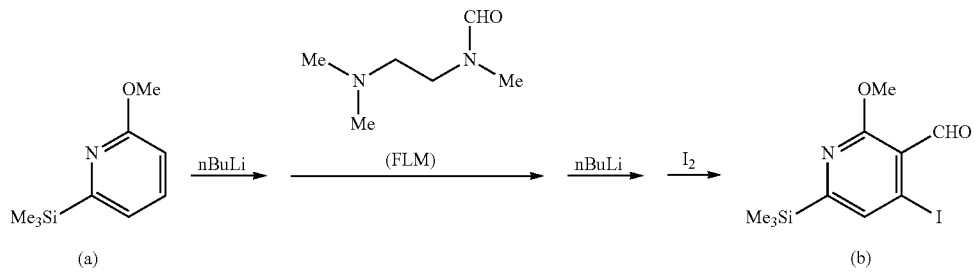

however, there is a possibility that it might become difficult to obtain 2-(dimethylamino)ethyl chloride, which is a starting material in the preparation of N-methyl-N-[2-(dimethylamino)ethyl]formamide (FLM) used in this method in the future as it can serve as a starting material in the preparation of a chemical weapon.

On the other hand, alkoxyalkylformamide (formula I) analogs used as formylation reagents of the present invention have been reported (Patent Publications 2 and 3), but these have only been used as starting materials for 6-aminopenicillanic acid or disclosed as a by-product in electrosynthesizing a butanetetracarboxylic acid derivative, and there has been no description at all of their use as formylation reagents.

[Patent Publication 1] WO 02/066416
[Patent Publication 2] JP, B, 51-8955
[Patent Publication 3] JP, A, 2004-514786

DISCLOSURE OF INVENTION

Problems to be Solved by the Invention

It is therefore an object of the present invention to efficiently supply CPT, which is a starting compound for irinotecan hydrochloride and for various types of camptothecin derivatives, and camptothecin analogs such as 7-ethyl-10-hydroxycamptothecin (SN-38), which is an important intermediate for the synthesis of irinotecan hydrochloride by practical total synthesis.

Means for Solving the Problems

In order to solve the above-mentioned problems, the present inventors have developed novel formylation reagents for a methoxypyridine derivative used in preparation of (S)-4-ethyl-3,4,6,7,8,10-hexahydro-4-hydroxy-1H-pyrano[3,4-f]indolizin-3,6,10-trione (hereinafter, referred to as compound (k)), which corresponds to the CDE ring moiety of the CPT skeleton, for the purpose of improving the preparation process, and have found that use of the formylation reagents enables formylation of the methoxypyridine derivative and subsequent iodination to be carried out in high yield, and the present invention has thus been accomplished.

Namely, the present invention relates to a process for preparing a tricyclic ketone (k), represented by the formula below, for synthesizing camptothecin analogs

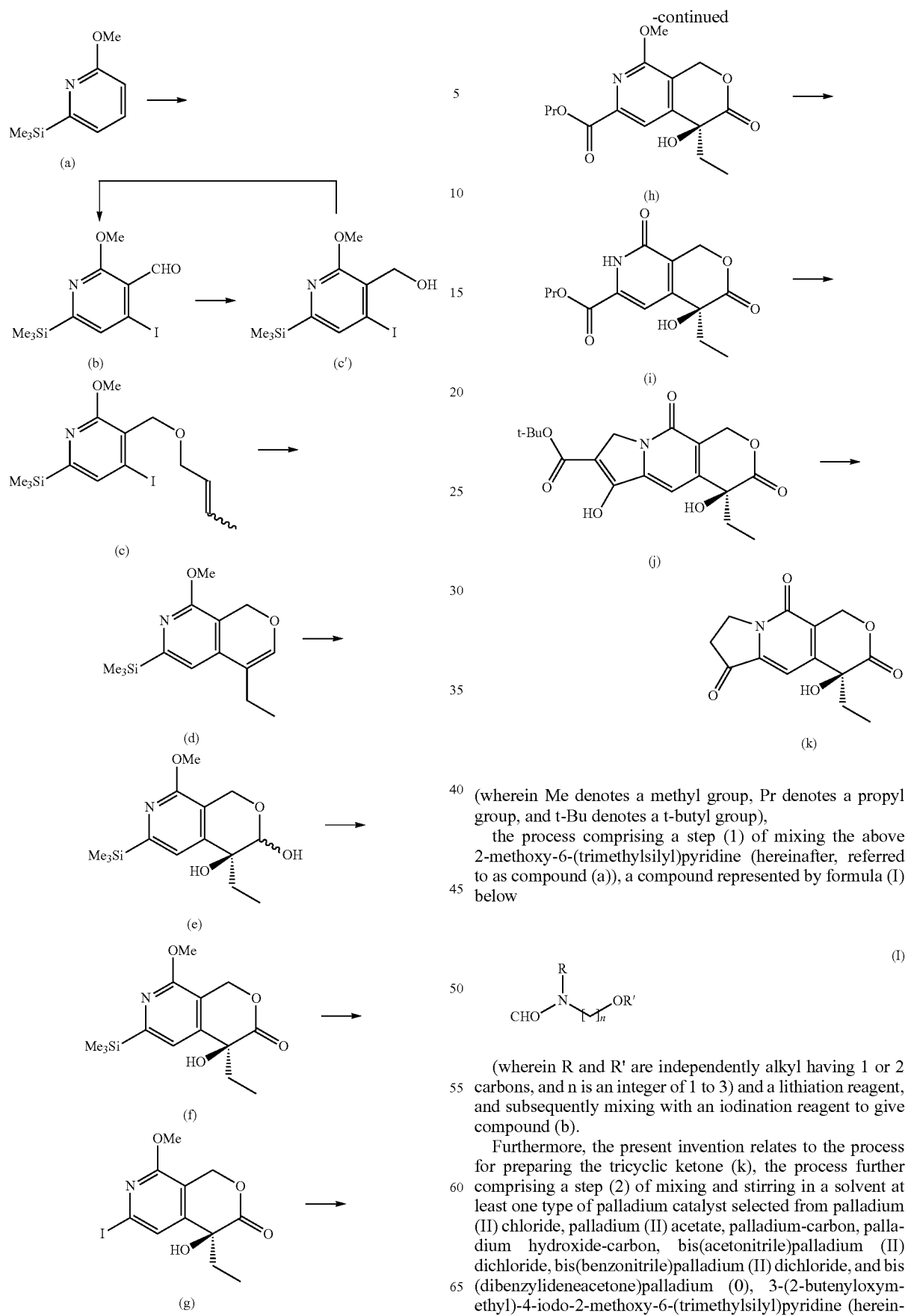

(wherein Me denotes a methyl group, Pr denotes a propyl group, and t-Bu denotes a t-butyl group), the process comprising a step (1) of mixing the above 2-methoxy-6-(trimethylsilyl)pyridine (hereinafter, referred to as compound (a)), a compound represented by formula (I) below

(I)

(wherein R and R' are independently alkyl having 1 or 2 carbons, and n is an integer of 1 to 3) and a lithiation reagent, and subsequently mixing with an iodination reagent to give compound (b).

Furthermore, the present invention relates to the process for preparing the tricyclic ketone (k), the process further comprising a step (2) of mixing and stirring in a solvent at least one type of palladium catalyst selected from palladium (II) chloride, palladium (II) acetate, palladium-carbon, palladium hydroxide-carbon, bis(acetonitrile)palladium (II) dichloride, bis(benzonitrile)palladium (II) dichloride, and bis (dibenzylideneacetone)palladium (0), 3-(2-butenyloxymethyl)-4-iodo-2-methoxy-6-(trimethylsilyl)pyridine (hereinafter, referred to as compound (c)), a base, and a quaternary ammonium salt to give 4-ethyl-8-methoxy-6-trimethylsilyl-1H-pyrano[3,4-c]pyridine (hereinafter, referred to as compound (d)).

The present invention relates to the process for preparing the tricyclic ketone (k), wherein in step (1) the compound represented by formula (I) in which n is 2 is used.

Furthermore, the present invention relates to the process for preparing the tricyclic ketone (k), wherein in step (1) the lithiation reagent is n-butyllithium.

Moreover, the present invention relates to the process for preparing the tricyclic ketone (k), wherein in step (2) the solvent is a water-containing solvent.

The present invention also relates to the process for preparing the tricyclic ketone (k), wherein in step (2) the solvent is a mixture of a nitrile-type organic solvent and water.

Furthermore, the present invention relates to the process for preparing the tricyclic ketone (k), wherein in step (2) the solvent is a mixture of an ether-type organic solvent, a nitrile-type organic solvent, and water.

The present invention relates to the use of the tricyclic ketone (k) obtained by the above-mentioned process in the preparation of camptothecin analogs.

Furthermore, the present invention relates to a process for synthesizing camptothecin analogs, the process involving reacting the tricyclic ketone (k) obtained by the above-mentioned process with 2'-amino-5'-hydroxypropiophenone.

Moreover, the present invention relates to a process for preparing formylated methoxypyridine derivatives by reacting methoxypyridine derivatives with a compound (alkoxyalkylformamide) represented by formula (I)

(I)

(wherein R and R' are independently alkyl having 1 or 2 carbons, and n is an integer of 1 to 3).

The present invention relates to the process for preparing formylated methoxypyridine derivatives, wherein a compound of formula (I) in which n is 2 is used. Furthermore, the present invention relates to the process for preparing the formylated methoxypyridine derivatives, wherein it is carried out in the presence of n-butyllithium.

Moreover, the present invention relates to the process for preparing the formylated methoxypyridine derivatives, wherein it is a process for preparing a compound represented by formula (II),

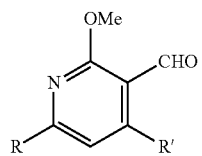
(II)

(wherein R is a halogen, hydrogen atom, or trimethylsilyl group, and R' is a halogen, alkyl, trimethylsilyl, or thioalkyl group), and an ortho position to a formyl group introduced by the above-mentioned preparation process is substituted with an electrophile.

Furthermore, the present invention relates to alkoxyalkylformamides represented by formula (I)

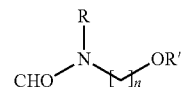
(I)

(wherein R and R' are independently alkyl having 1 or 2 carbons and n is an integer of 1 to 3, but excluding one in which n is 1 and R and R' are both methyl and one in which n is 2 and R and R' are both ethyl).

Effects of the Invention

Not only can the alkoxyalkylformamides [formula (I)] of the present invention be used effectively as formylation reagents for a methoxypyridine derivative, but it is also possible to efficiently supply the tricyclic ketone (k) as an intermediate of camptothecin analogs.

Furthermore, by use of the present invention, the endo/exo ratio of compound (d), which is an intermediate for the tricyclic ketone (k), can be increased effectively. By selecting as a palladium catalyst for the process at least one type from palladium (II) chloride, palladium (II) acetate, palladium-carbon, palladium hydroxide-carbon, bis(acetonitrile)palladium (II) dichloride, bis(benzonitrile)palladium (II) dichloride, and bis(dibenzylideneacetone)palladium (0), the endo/exo ratio and the yield can be improved.

BEST MODE FOR CARRYING OUT THE INVENTION

Preparation of the Tricyclic Ketone (K) is carried out via the synthetic route below.

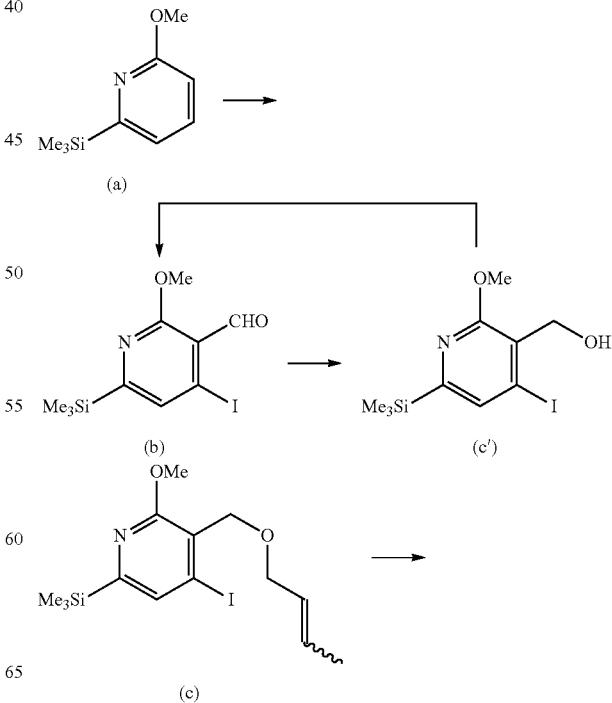

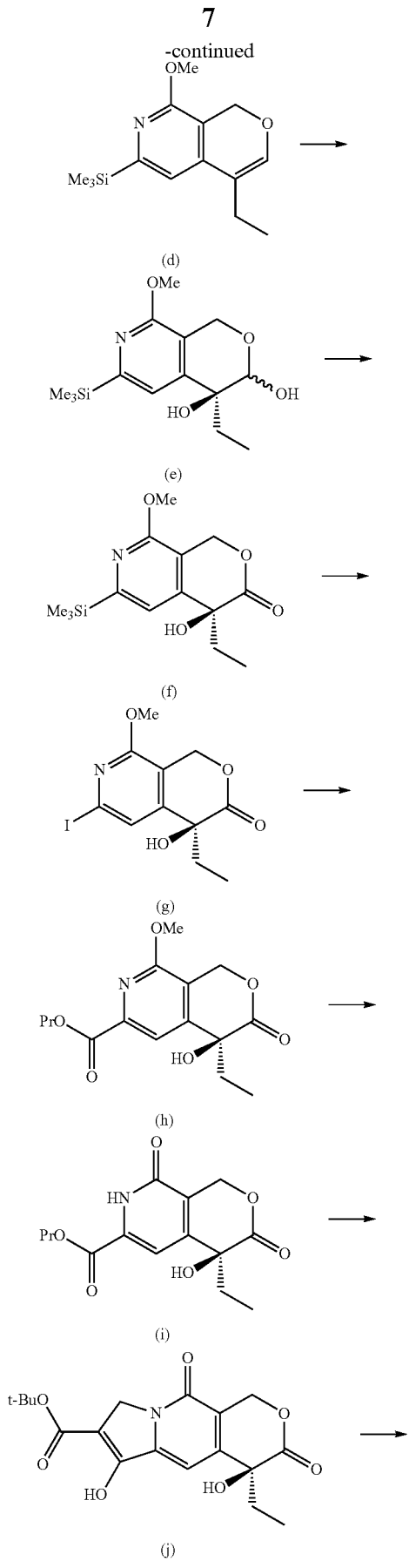

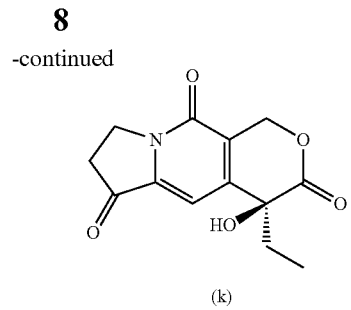

In the formula, Me denotes a methyl group, Pr denotes a propyl group, and t-Bu denotes a t-butyl group. With regard to compound (a), which serves as a starting compound in the above-mentioned synthetic route, it may be synthesized by the Curran route (Josien, H.; Ko, S. B.; Bom, D.; Curran, D. P., Chem. Eur. J. 1998, 4, 67-83, "A General Synthetic Approach to the (20S)-Camptothecin Family of Antitumor Agents by a Regiocontrolled Cascade Radical Cyclization of Aryl Isonitriles"), obtained by chemical modifications of compound (a) analogs, or obtained by isolation and purification from various types of natural materials and the like, or it may be a natural material itself containing compound (a).

A preferred process for synthesizing the tricyclic ketone (k) in the above-mentioned synthetic route comprises step (i) or steps (i) and (iv) among the steps below:

(i) a step of synthesizing compound (b) by mixing 2-methoxy-6-trimethylsilylpyridine (compound (a)) with a lithiation reagent, an alkoxyalkylformamide [formula (I)], and an iodination reagent, (ii) a step of synthesizing compound (c) by mixing compound (b) with crotyl alcohol, triethylsilane, and an acid, and reacting the mixture without a solvent, (iii) a step of obtaining compound (b) by mixing 4-iodo-3-hydroxymethyl-2-methoxy-6-(trimethylsilyl)pyridine (hereinafter, referred to as compound (c')), which is a by-product in step (ii), with an oxidizing agent and in some cases a base, (iv) a step of synthesizing compound (d) by mixing and stirring compound (c) in the presence of a palladium catalyst, a base, and a quaternary ammonium salt in a solvent, (v) a step of synthesizing (S)-4-ethyl-3,4-dihydro-8-methoxy-6-trimethylsilyl-1H-pyrano[3,4-c]pyridine-3,4-diol (hereinafter, referred to as compound (e)) from compound (d) with an osmium catalyst, a co-oxidizing agent, a base, an asymmetric reagent, and methanesulfonamide, (vi) a step of synthesizing (S)-4-ethyl-3,4-dihydro-4-hydroxy-8-methoxy-6-trimethylsilyl-1H-pyrano[3,4-c]pyridin-3-one (hereinafter, referred to as compound (f)) by mixing compound (e) with a base and iodine, and heating the mixture in an alcohol-water mixture under reflux, (vii) a step of synthesizing (S)-4-ethyl-3,4-dihydro-4-hydroxy-6-iodo-8-methoxy-1H-pyrano[3,4-c]pyridin-3-one (hereinafter, referred to as compound (g)) by mixing compound (f) with a desilylation-iodination reagent, (viii) a step of chemically purifying compound (g) by adding a basic aqueous solution such as a sodium hydroxide solution to make the solution alkaline, washing with an organic solvent such as chloroform, subsequently making the aqueous layer acidic, and extracting with an organic solvent such as chloroform, (ix) a step of optically purifying compound (g) by dissolving compound (g) in a high polarity solvent such as chloroform, adding a low polarity solvent such as n-hexane, filtering the resulting precipitate, and concentrating the filtrate, (x) a step of obtaining (S)-4-ethyl-3,4-dihydro-4-hydroxy-8-methoxy-3-oxo-1H-pyrano[3,4-c]pyridine-6-carboxylic acid propyl ester (hereinafter, referred to as compound (h)) by mixing compound (g) with a palladium catalyst and a base and reacting the mixture in 1-propanol under a carbon monoxide atmosphere, (xi) a step of synthesizing (S)-4-ethyl-3,4,7,8-tetrahydro-4-hydroxy-3,8-dioxo-1H-pyrano[3,4-c]pyridine-6-carboxylic acid propyl ester (hereinafter, referred to as compound (i)) by reacting compound (h) with a demethylation reagent at room temperature, and (xii) a step of synthesizing (S)-4-ethyl-3,4,8,10-tetrahydro-4,6-dihydroxy-3,10-dioxo-1H-pyrano[3,4-f]indolizine-7-carboxylic acid 1,1-dimethylethyl ester (hereinafter, referred to as compound (j)) by reacting compound (i) with t-butyl acrylate and a base. Compound (k) may be synthesized from compound (j) via the above-mentioned Curran route.

Furthermore, (xiii) in a step of obtaining SN-38 from compound (k) and 2'-amino-5'-hydroxypropiophenone, SN-38 can favorably be obtained by the reaction under an inert gas atmosphere.

The above-mentioned 13 steps are now explained in further detail.

In (i), compound (a) is dissolved in a solvent, and a lithiation reagent, a formylation reagent, and an iodination reagent are added to the solution and it is stirred to give compound (b). As the solvent, tetrahydrofuran (THF), diethyl ether, toluene, hexane, heptane and the like may be used, and from the viewpoint of solubility and reactivity THF is particularly preferable.

As the lithiation reagent, any one may suitably be used if it is conventionally used. Specific examples of the lithiation reagent include n-butyllithium, s-butyllithium, t-butyllithium, lithium diisopropylamide (LDA), and lithium bis(trimethylsilyl)amide (LiHMDS), and particularly from the viewpoint of ease of handling and reactivity, n-butyllithium may suitably be used.

The amount of lithiation reagent may be determined appropriately according to the reagent, and in case that n-butyllithium is used, it is used at 0.5 to 10 equivalents relative to compound (a), preferably 1 to 5 equivalents.

The reaction temperature for lithiation is a constant temperature in the range of −78° C. to 25° C., preferably −78° C. to 0° C., particularly preferably −30° C. to 0° C.

Specific examples of the formylation reagent used in the present invention include N-methoxymethyl-N-methylformamide (FMM), N-methoxyethyl-N-methylformamide (FMO), N-ethoxyethyl-N-methylformamide (FEO), N-methoxyethyl-N-ethylformamide (FEA), N-ethoxyethyl-N-ethylformamide (FEE), and N-ethoxypropyl-N-methylformamide (FEP), and when taking into consideration the subsequent iodination, FMO, FEO, FEA, or FEE may suitably be used.

With regard to the amount of formylation reagent, in case that FEO is used, it is 1 to 10 equivalents relative to compound (a), preferably 1 to 3 equivalents.

The reaction temperature for formylation is a constant temperature in the range of −78° C. to 25° C., preferably −78° C. to 0° C., particularly preferably −30° C. to 0° C.

As the iodination reagent, iodine, N-iodosuccinimide (NIS), 1,2-diiodoethane and the like may be used, and from the viewpoint of cost and reactivity iodine is particularly preferable.

The amount of iodination reagent is 1 to 10 equivalents relative to compound (a), preferably 1 to 5 equivalents.

The reaction temperature for iodination is in the range of −78° C. to 25° C., preferably −78° C. to 0° C. The reaction may be carried out at a constant temperature or may be carried out while raising the temperature within these ranges.

In (ii), compound (c) is obtained by adding crotyl alcohol, triethylsilane, and an acid to compound (b) and stirring without employing a solvent.

The amount of crotyl alcohol is 1 to 10 equivalents relative to compound (b), preferably 2 to 5 equivalents.

The amount of triethylsilane is 1 to 10 equivalents relative to compound (b), preferably 1 to 4 equivalents.

As the acid, trifluoroacetic acid (TFA), sulfuric acid, methanesulfonic acid, hydrochloric acid and the like may be used, and from the viewpoint of reactivity TFA is particularly preferable.

With regard to the amount of acid, in case that TFA is used, it is 1 to 20 equivalents relative to compound (b), preferably 5 to 15 equivalents.

In (iii), compound (b) is obtained by dissolving compound (c'), which is a by-product in (ii), in a solvent, adding an oxidizing agent, and in some cases a base, and stirring.

As the solvent, any one may suitably be used if it is conventionally used. Examples of such a solvent include dichloromethane, chloroform, acetonitrile, toluene, and n-hexane, and from the viewpoint of reactivity toluene and n-hexane are particularly preferable.

Examples of the oxidizing agent include manganese dioxide, Dess-Martin reagent (Dess-Martin Periodinane), Jones reagent ($Na_2Cr_2O_7$—$H_2SO_4$), PCC, PDC, DMSO-oxalyl chloride-triethylamine (Swern oxidation), and a TEMPO-hypochlorite; the TEMPO-hypochlorite is particularly preferable, and TEMPO-sodium hypochlorite is more preferable.

With regard to the amount of oxidizing agent, for example, in the case of TEMPO-sodium hypochlorite, TEMPO is used at 0.001 to 0.1 equivalents relative to compound (c'), preferably 0.005 to 0.02 equivalents. Sodium hypochlorite is used at 1 to 5 equivalents, preferably 1 to 2 equivalents.

As the base, any one may suitably be used if it is conventionally used. Examples of such a base include sodium hydrogen carbonate, sodium carbonate, potassium carbonate, calcium carbonate, sodium hydroxide, potassium hydroxide, calcium hydroxide, and triethylamine, and sodium hydrogen carbonate is particularly preferable.

With regard to the amount of base, for example, in the case of sodium hydrogen carbonate, sodium hydrogen carbonate is 1 to 10 equivalents relative to compound (c'), preferably 2 to 4 equivalents. With regard to the reaction temperature, in case that TEMPO-sodium hypochlorite is used as the oxidizing agent, it is in the range of −20° C. to 30° C., and in order to particularly suppress a side reaction it is preferably −20° C. to 10° C.

Furthermore, with regard to the reaction time, in case that TEMPO-sodium hypochlorite is used as the oxidizing agent, it is in the range of 0.1 to 10 hours, preferably 0.5 to 5 hours.

In (iv), compound (d) is obtained by dissolving compound (c) in a solvent, adding a palladium catalyst, a base, and a quaternary ammonium salt, and heating under reflux.

As the solvent, a nitrile-type solvent such as acetonitrile or propionitrile, an ether-type solvent such as tetrahydrofuran (THF), diisopropyl ether (IPE), diethyl ether, or 1,2-dimethoxyethane, toluene, water and the like may be used. Particularly from the viewpoint of reactivity a mixture in which any of an ether-type solvent, a nitrile-type solvent, and water are combined is preferable, a mixture of IPE, acetonitrile and water is particularly preferable, and a mixture of acetonitrile and water is more particularly preferable.

As the palladium catalyst, palladium (II) chloride, palladium (II) acetate, palladium-carbon, palladium hydroxide-carbon, bis(acetonitrile)palladium (II) dichloride, bis(benzonitrile)palladium (II) dichloride, bis(dibenzylideneacetone)palladium (0) and the like may suitably be used, and from the viewpoint of reactivity palladium (II) chloride is particularly preferable.

The amount of palladium catalyst is 0.01 to 1 equivalents relative to compound (c), preferably 0.05 to 0.2 equivalents.

As the base, any one may suitably be used if it is conventionally used. Examples of such a base include sodium carbonate, potassium carbonate, calcium carbonate, cesium carbonate, triethylamine (TEA), N,N-diisopropylethylamine (DIPEA), sodium hydroxide, and potassium hydroxide, and TEA and DIPEA may be used particularly suitably.

With regard to the amount of base, for example, in the case of TEA, it is 1 to 20 equivalents relative to compound (c), preferably 5 to 10 equivalents.

As the quaternary ammonium salt, any one may suitably be used if it is conventionally used. Examples of such quaternary ammonium salts include a tetrabutylammonium halide and a benzyltriethylammonium halide, and tetrabutylammonium bromide is particularly preferable.

With regard to the amount of quaternary ammonium salt, for example, in the case of tetrabutylammonium bromide, it is 0.1 to 3 equivalents relative to compound (c), preferably 0.5 to 1.5 equivalents.

Furthermore, with regard to the reaction time, in case that a mixture of acetonitrile, IPE and water is used, it is in the range of 0.1 to 10 hours, preferably 0.5 to 5 hours.

In (v), compound (e) is obtained by dissolving compound (d) in a mixture of alcohol and water, adding an osmium catalyst, a co-oxidizing agent, an asymmetric reagent, a base, and methanesulfonamide, and stirring.

Examples of the alcohol include methanol, ethanol, 1-propanol, 2-propanol (IPA), 1-butanol, 2-butanol, and t-butyl alcohol. From the viewpoint of reactivity t-butyl alcohol is particularly preferable.

As the osmium catalyst, osmium tetraoxide, potassium osmate (VI) and the like may be used suitably, and from the viewpoint of ease of handling potassium osmate (VI) is particularly preferable.

The amount of osmium catalyst is 0.001 to 0.1 equivalents relative to compound (d), preferably 0.002 to 0.01 equivalents.

As the co-oxidizing agent, potassium hexacyanoferrate (III), 4-methylmorpholine N-oxide (NMO), etc. may be used suitably, and from the viewpoint of reactivity potassium hexacyanoferrate (III) is particularly preferable.

With regard to the amount of co-oxidizing agent, for example, in the case of potassium hexacyanoferrate (III), it is 1 to 10 equivalents relative to compound (d), preferably 2 to 5 equivalents.

Examples of the asymmetric reagent include $(DHQD)_2$PYR, $(DHQD)_2$PHAL, and $(DHQD)_2$AQN, and from the viewpoint of optical yield $(DHQD)_2$PYR is particularly preferable.

With regard to the amount of asymmetric reagent, for example, in the case of $(DHQD)_2$PYR, it is 0.005 to 0.1 equivalents relative to compound (d), preferably 0.01 to 0.05 equivalents.

As the base, sodium carbonate, potassium carbonate, calcium carbonate, cesium carbonate, sodium hydroxide, potassium hydroxide and the like may be used, and from the viewpoint of reactivity potassium carbonate is particularly preferable.

With regard to the amount of base, for example, in the case of potassium carbonate, it is 1 to 20 equivalents relative to compound (d), preferably 4 to 10 equivalents.

The amount of methanesulfonamide is 0.1 to 5 equivalents relative to compound (d), preferably 0.5 to 2 equivalents.

The reaction temperature is in the range of −20° C. to 30° C., preferably −10° C. to 10° C.

In (vi), compound (f) is obtained by dissolving compound (e) in a solvent, adding a base and iodine, and heating under reflux.

Examples of the solvent include methanol, ethanol, 1-propanol, 2-propanol (IPA), and water, and from the viewpoint of reactivity a mixture of methanol and water is particularly preferable.

As the base, a conventionally used base may be used suitably. Examples of such a base include sodium carbonate, potassium carbonate, calcium carbonate, cesium carbonate, sodium hydroxide, and potassium hydroxide, and calcium carbonate is particularly preferable.

With regard to the amount of base, for example, in the case of calcium carbonate, it is 1 to 10 equivalents relative to compound (e), preferably 2 to 5 equivalents.

With regard to the amount of iodine, it is 1 to 10 equivalents relative to compound (e), preferably 3 to 5 equivalents.

Furthermore, the reaction time is in the range of 0.5 to 20 hours, more preferably 1 to 5 hours.

In (vii), compound (g) is obtained by dissolving compound (f) in a solvent, and reacting in the presence of iodine-silver trifluoroacetate (hereinafter, referred to as $I_2$—$CF_3COOAg$) or N-chlorosuccinimide-sodium iodide (hereinafter, referred to as NCS-NaI).

With regard to the solvent, in the case of $I_2$—$CF_3COOAg$, dichloromethane, carbon tetrachloride, chloroform and the like are suitable, and dichloromethane is particularly preferable. In the case of NCS-NaI, acetic acid, acetonitrile and the like may be used, and from the viewpoint of reactivity acetic acid is particularly preferable.

With regard to the amount of $I_2$—$CF_3COOAg$, $I_2$ is 1 to 10 equivalents relative to compound (f), preferably 2 to 4 equivalents. $CF_3COOAg$ is 1 to 10 equivalents, preferably 2 to 4 equivalents.

With regard to the amount of NCS-NaI, NCS is 1 to 20 equivalents relative to compound (f), preferably 5 to 8 equivalents. NaI is 1 to 20 equivalents, preferably 5 to 8 equivalents.

With regard to the temperature during the reaction, in case that $I_2$—$CF_3COOAg$ is used, it is 10° C. to 60° C., preferably 20° C. to 40° C. In case that NCS-NaI is used, it is 20° C. to the reflux temperature, preferably 50° C. to 80° C.

Furthermore, the reaction time is in the range of 5 to 48 hours, preferably 15 to 24 hours.

In (viii), for example, by adding to compound (g) a basic solvent such as a 0.2 N aqueous solution of sodium hydroxide and stirring, compound (g) becomes a lactone ring-opened form (compound (I):

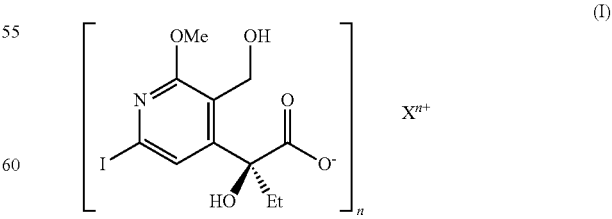

(wherein Me denotes a methyl group, Et denotes an ethyl group, X denotes an alkali metal or an alkaline earth metal, and n denotes 1 or 2)), and dissolves in the basic aqueous solution. When this solution is washed with an organic solvent, neutral and basic materials move to the organic layer. After the organic layer is separated, the aqueous layer is made acidic using an acid and extracted with an organic solvent, thus recovering compound (g) with good purity.

The concentration of basic solvent is in the range of 0.01 to 5 N, preferably 0.1 to 1 N. It is more preferably 0.2 to 0.5 N.

Examples of the base include potassium hydroxide, calcium hydroxide, sodium hydroxide, potassium carbonate, and sodium carbonate, and sodium hydroxide is particularly preferable.

As the organic solvent, any one may suitably be used if it is conventionally used. Examples of such a solvent include dichloromethane, chloroform, ethyl acetate, toluene, diethyl ether, and diisopropyl ether, and dichloromethane and chloroform are particularly preferable.

Examples of the acid include hydrochloric acid, sulfuric acid, nitric acid, acetic acid, phosphoric acid, and trifluoroacetic acid, and hydrochloric acid is particularly preferable.

In (ix), when compound (g) is dissolved in a high polarity solvent and a low polarity solvent is added, crystals are precipitated. The crystals are filtered off, and the filtrate is concentrated and dried under reduced pressure. The resulting crystals are racemic, and a more optically purified compound (g) is obtained as a residue.

As the high polarity solvent, chloroform, dichloromethane, ethyl acetate, methanol, ethanol, propanol and the like may be used, and chloroform is particularly preferable. With regard to the amount of high polarity solvent, for example, in the case of chloroform, it is in the range of 0.5 to 10 mL relative to 1 g of compound (g), preferably 1 to 5 mL, particularly preferably 3 to 5 mL.

Examples of the low polarity solvent include n-hexane, n-heptane, and diethyl ether, and n-hexane is particularly preferable.

With regard to the high polarity solvent:low polarity solvent ratio, for example, in the case of chloroform:n-hexane, it is in the range of 10:1 to 1:20, preferably 5:1 to 1:5.

The temperature of the crystallization procedure is preferably no greater than 30° C., particularly preferably 0° C. to 30° C.

In (x), compound (h) is obtained by dissolving compound (g) in 1-propanol, adding a palladium catalyst and a base, and reacting under an atmosphere of carbon monoxide gas.

As the palladium catalyst, palladium (II) acetate, tetrakis (triphenylphosphine)palladium (0), dichlorobis(triphenylphosphine)palladium(II), palladium (II) chloride and the like may suitably be used, and from the viewpoint of reactivity palladium (II) acetate is particularly preferable.

The amount of palladium catalyst is 0.005 to 0.5 equivalents relative to compound (g), preferably 0.01 to 0.1 equivalents.

As the base, any one may suitably be used if it is conventionally used. Examples of such a base include sodium carbonate, potassium carbonate, calcium carbonate, cesium carbonate, triethylamine (TEA), N,N-diisopropylethylamine (DIPEA), sodium hydroxide, and potassium hydroxide, and potassium carbonate, TEA, and DIPEA are particularly suitably used. With regard to the amount of base, for example, in the case of potassium carbonate, it is 1 to 20 equivalents relative to compound (g), preferably 4 to 10 equivalents.

The reaction temperature is in the range of 20° C. to the reflux temperature, preferably 50° C. to the reflux temperature.

In (xi), compound (i) is obtained by dissolving compound (h) in a solvent, adding a demethylation reagent, and reacting at room temperature.

As the solvent, acetonitrile, chloroform, dichloromethane, toluene and the like may be used, and acetonitrile is particularly preferable.

Examples of the demethylation reagent include chlorotrimethylsilane-sodium iodide, iodotrimethylsilane, hydroiodic acid, and hydrobromic acid, and from the viewpoint of reactivity chlorotrimethylsilane-sodium iodide is particularly preferable.

With regard to the amount of demethylation reagent, for example, in the case of chlorotrimethylsilane-sodium iodide, chlorotrimethylsilane and sodium iodide are both in the range of 1 to 10 equivalents relative to compound (h), preferably 2 to 5 equivalents.

In (xii), compound (i) is dissolved in a solvent, a base is added, and it is stirred under an inert gas. t-Butyl acrylate is added dropwise to the resulting mixture, and it is stirred under an inert gas, thus giving compound (j).

With regard to the solvent, dimethyl sulfoxide (DMSO), N,N-dimethylformamide (DMF), N,N-dimethylacetamide (DMA) and the like may be used suitably, and from the viewpoint of reactivity DMSO is particularly preferable.

As the base, potassium carbonate, sodium carbonate, sodium hydroxide, potassium hydroxide and the like may be used, and potassium carbonate is particularly preferable.

With regard to the amount of base added, for example, in the case of potassium carbonate, it is 1 to 20 equivalents relative to compound (i), preferably 2 to 5 equivalents.

As the inert gas, a noble gas such as argon, helium, neon, krypton, xenon, or radon or any gas that has low reactivity such as nitrogen may be used, and in terms of cost argon and nitrogen are preferable.

The amount of t-butyl acrylate is 1 to 20 equivalents relative to compound (i), preferably 8 to 12 equivalents.

The reaction temperature is in the range of 20° C. to 80° C., preferably 40° C. to 60° C.

Furthermore, the reaction time is 5 to 48 hours, and in order to prevent decomposition of the compound (j) thus formed, it is particularly preferably less than 24 hours. Compound (k) may be synthesized by the above-mentioned Curran route from compound (j).

In (xiii), SN-38 is obtained by dissolving compound (k) and 2'-amino-5'-propiophenone in a solvent, adding an acid, and heating and stirring under an atmosphere of an inert gas.

As the solvent, toluene, acetic acid and the like may be used suitably, and a mixture of toluene and acetic acid is particularly preferable.

As the inert gas, a noble gas such as argon, helium, neon, krypton, xenon, or radon or any gas that has low reactivity such as nitrogen may be used, and in terms of cost argon and nitrogen are preferable.

As the acid, toluenesulfonic acid, methanesulfonic acid, trifluoroacetic acid and the like may be used, and from the viewpoint of reactivity toluenesulfonic acid is particularly preferable.

With regard to the amount of acid, for example, in the case of toluenesulfonic acid, it is 1 to 100 mg relative to 1 g of compound (k), preferably 10 to 30 mg.

The amount of 2'-amino-5'-propiophenone is 1 to 3 equivalents relative to compound (k), preferably 1 to 1.5 equivalents.

The reaction temperature is in the range of 50° C. to the reflux temperature, preferably in the range of 80° C. to the reflux temperature.

The alkoxyalkylformamide [formula (I)] of the present invention is not only suitable for formylation of compound (a) but may also be used in formylation of general methoxypyridine derivatives, and it is possible to prepare formylated methoxypyridine derivatives in high yield.

Examples of methoxypyridine derivatives that can be formylated with the alkoxyalkylformamide [formula (I)] of the present invention include, in addition to compound (a), 2-methoxypyridine, 2-chloro-6-methoxypyridine, 2-alkyl-6-methoxypyridine, 2-methoxy-5-(trimethylsilyl)pyridine, 5-chloro-2-methoxypyridine, and 5-alkyl-2-methoxypyridine. The term alkyl referred to here means lower alkyl having 1 to 5 carbons.

Furthermore, after formylation of a methoxypyridine derivative using the alkoxyalkylformamide [formula (I)] of the present invention, it is possible, using various types of electrophile, to selectively add a substituent to the ortho position of the formyl group that has been introduced.

Examples of electrophiles include, in addition to iodine, methyl iodide, chlorotrimethylsilane, hexachloroethane, tetrabromomethane, and dimethyldisulfide.

The present invention is illustrated further in detail below by reference to Examples, but the present invention is not limited thereto.

EXAMPLES

Example 1

Synthesis of compound (b) from compound (a) was studied with the alkoxyalkylformamides [formula (I)] of the present invention.

In a reaction vessel filled with nitrogen gas or argon gas, compound (a) (1.00 g, 5.52 mmol) was dissolved in dry tetrahydrofuran (about 13 mL) and cooled to around −30° C. to −15° C. n-Butyllithium (1.6 mol/L n-hexane solution; 4.8 mL, 7.73 mmol, 1.4 equivalents) was added dropwise to the resulting solution, and stirred at the same temperature for 1 hour. Subsequently, an alkoxyalkylformamide (1.2 equivalents) shown in Table 2 was added dropwise, and the mixture was stirred at the same temperature for 2 hours. Part of the reaction solution was sampled, quenched with water, and then extracted with ethyl acetate. Part of the resulting organic layer was injected into an HPLC, and the progress of the reaction was checked. The HPLC operating conditions were the same as in a quantitative determination method for compound (b).

n-Butyllithium (1.6 mol/L n-hexane solution; 7.0 mL, 11.0 mmol, 2.0 equivalents) was added dropwise to the resulting mixture and stirred at around −30° C. to −15° C. for 3 hours. Subsequently, a dry tetrahydrofuran solution (5.5 mL) of iodine (3.64 g, 14.4 mmol, 2.6 equivalents) was added dropwise at around −60° C. to −45° C., and the mixture was stirred at the same temperature for 30 minutes.

An aqueous solution of sodium sulfite (appropriate amount, until the color of iodine disappeared) and n-hexane (appropriate amount) were added into the resulting mixture and stirred, the organic layer was then separated and concentrated to dryness, and the resulting residue was analyzed by an HPLC method. The results are given in Table 1.

Quantitative Determination Method for Compound (b)

About 20 mg of a test sample was precisely weighed and dissolved in acetonitrile to accurately make 100 mL, thus giving a sample solution. About 20 mg of standard compound (b) (column purified product: known purity) was precisely weighed and dissolved in acetonitrile to accurately make 100 mL, thus giving a standard solution. 10 μL each of the sample and the standard solution were tested by a liquid chromatographic method in accordance with a Japanese Pharmacopeia General Test Procedure under the operating conditions below.

The peak areas of PM obtained from the sample and from the standard solution were measured and the content was determined by the formula below.

Content(%) of compound$(b) = At \times Ws \times P/(As \times Wt)$

At: peak area of PM obtained from sample solution
As: peak area of PM obtained from standard solution
Wt: sampling weight of test PM (mg)
Ws: sampling weight of standard PM (mg)
P: purity of standard PM(%)

HPLC operating conditions
Column: Inertsil ODS-2, 4.6 mm ID×150 mm
Mobile phase: MeCN—0.01 mol/L$KH_2PO_4$ mixture (5:1)
Measurement wavelength: 254 nm
Flow rate: about 1 mL/min
Measurement temperature: constant temperature at around 40° C.

TABLE 1

| | | Formylation %[1] | Iodination %[1] | | Yield[2] |
|---|---|---|---|---|---|
| Run | Reagent | MTPC | PM | IMTP | % |
| 1 | FLM | 89.9 | 59.7 | 6.5 | 55 |
| 2 | FMM | 74.8 | 5.8 | 15.2 | —[3] |
| 3 | FMO | 81.9 | 55.3 | 10.1 | 49 |
| 4 | FEO | 85.3 | 61.4 | 5.4 | 52 |
| 5 | FEA | 82.0 | 57.7 | 7.8 | 52 |
| 6 | FEE | 82.8 | 58.2 | 5.0 | 52 |
| 7 | FEP | 83.6 | 29.0 | 6.1 | —[3] |

[1]HPLC area percentage
[2]Calculated based on quantitative determination by HPLC
[3]Not calculated In Table 1 above, 'FLM' in run 1 means N-methyl-N-[2-(dimethylamino)ethyl]formamide, which is conventionally used as a formylation reagent, and the abbreviations for the reagents of run 2 to run 7 mean the alkoxyalkylformamides described in Table 2 below.

TABLE 2

Alkoxyalkylformamides $$\text{CHO}-\underset{\underset{\text{R}}{|}}{\text{N}}-(\text{CH}_2)_n-\text{OR}'$$

| Compound name | n | R | R' |
|---|---|---|---|
| FMM | 1 | Me | Me |
| FMO | 2 | Me | Me |
| FEO | 2 | Me | Et |
| FEA | 2 | Et | Me |
| FEE | 2 | Et | Et |
| FEP | 3 | Me | Et |

As is clear from the results, the alkoxyalkylformamides of the present invention can be used effectively as a formylation reagent, and exhibits a performance that is not inferior to the conventional FLM.

Example 2

A reaction was examined with the alkoxyalkylformamide [formula (I)] at around −15° C. to 0° C.

n-Butyllithium (1.6 M in n-hexane, 4.8 mL, 5.52×1.4 mmol) was added dropwise to a dry THF (13.2 mL) solution of 2-methoxy-6-(trimethylsilyl)pyridine (MTP, 1.00 g, 5.52 mmol) under an argon atmosphere at between −15° C. and 0° C. (this temperature was kept during the reaction), stirred for 1 hour, and a dry THF (1 mL) solution of FEO (0.868 g, 5.52×1.2 mmol) was then added dropwise and it was stirred for 1 hour. Subsequently, n-butyllithium (1.6 M in n-hexane, 7.0 mL, 5.52×2.0 mmol) was added dropwise and it was stirred for 1 hour, and a dry THF (5.5 mL) solution of iodine (3.64 g, 5.52×2.6 mmol) was then added dropwise and it was stirred for 30 minutes. After the temperature was raised to room temperature, 10% $Na_2SO_3$ (appropriate amount, until the iodine color disappeared) was added and stirred for 10 minutes, and followed by adding water, brine, and n-hexane (50 mL). The organic layer was separated, dried over $Na_2SO_4$, filtered, and then concentrated to dryness (40° C., 15 mmHg). The residue (1.80 g, yellow clear liquid) was subjected to quantitative determination by HPLC to thus determine the content (59.8%) and yield (58%) of PM. The quantitative determination and HPLC operating conditions were carried out by the same methods as in Example 1.

$^1$H-NMR (400 MHz, $CDCl_3$) δ: 0.30 (9H, s, TMS), 4.05 (3H, s, $CH_3O$), 7.67 (1H, s, pyridine-H), 10.19 (1H, s, CHO).

IR (liquid film) ($cm^{-1}$): 2955, 1697 (CHO), 1551, 1512, 1331, 1250, 1022, 837.

EI-MS (m/z): 335 $[M]^+$, 320 (100%)

By use of the alkoxyalkylformamides [formula (I)], the same level of yield of Example 1 was obtained at the reaction temperature of −15° C. to 0° C., which is closer to room temperature.

Example 3

It was investigated whether it was possible to introduce other substituents to methoxypyridine derivatives with electrophiles other than iodine after formylation by the alkoxyalkylformamide of the present invention. The reaction processes were described as follows.

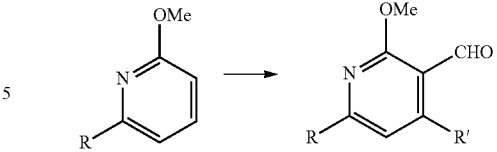

Synthesis of 2-methoxy-4-methyl-6-(trimethylsilyl) pyridine-3-carbaldehyde (Me-MTPC)

n-Butyllithium (1.6 M in n-hexane, 2.8 mL, 2.76×1.6 mmol) was added dropwise to a dry THF (6.6 mL) solution of 2-methoxy-6-(trimethylsilyl)pyridine (MTP, 0.500 g, 2.76 mmol) under an argon atmosphere at between −15° C. and 0° C. and stirred at the same temperature for 1 hour, and a dry THF (3 mL) solution of FEO (0.434 g, 2.76×1.2 mmol) was then added dropwise at the same temperature and stirred at the same temperature for 1 hour. Subsequently, n-butyllithium (1.6 M in n-hexane, 2.4 mL, 2.76×1.4 mmol) was added dropwise at the same temperature and stirred at the same temperature for 2 hours, it was then cooled to around −70° C., and a dry THF (3 mL) solution of methyl iodide (515 μL, 2.76×3.0 mmol) was added at one-portion and stirred at around −70° C. for 1 hour. The temperature was raised to room temperature, followed by adding water, brine, and n-hexane (50 mL). The organic layer was separated, dried over $Na_2SO_4$, filtered, and then concentrated to dryness. The residue was purified by medium pressure silica gel column chromatography (n-hexane:ethyl acetate=500:1), desired fractions were combined and concentrated to dryness, and Me-MTPC (0.331 g, 1.48 mmol, 54%) was obtained as a slightly yellow clear liquid.

$^1$H-NMR (400 MHz, $CDCl_3$) δ: 0.30 (9H, s, TMS), 2.56 (3H, s, $CH_3$), 4.05 (3H, s, $CH_3O$), 6.97 (1H, s, aromatic-H), 10.54 (1H, s, CHO).

IR (liquid film) ($cm^{-1}$): 2955, 1670 (CHO), 1547, 1339, 1245, 1092, 841.

EI-MS (m/z): 223 $[M]^+$, 208 (100%)

Synthesis of 2-methoxy-4,6-bis(trimethylsilyl)pyridine-3-carbaldehyde (TMS-MTPC)

n-Butyllithium (1.6 M in n-hexane, 2.8 mL, 2.76×1.6 mmol) was added dropwise to a dry THF (6.6 mL) solution of 2-methoxy-6-(trimethylsilyl)pyridine (MTP, 0.500 g, 2.76 mmol) under an argon atmosphere at between −15° C. and 0° C. (this temperature was kept during the reaction) and stirred for 1 hour, and a dry THF (2 mL) solution of FEO (0.434 g, 2.76×1.2 mmol) was then added dropwise and stirred for 1 hour. Subsequently, n-butyllithium (1.6 M in n-hexane, 2.4 mL, 2.76×1.4 mmol) was added dropwise and stirred for 1 hour, and a dry THF (3 mL) solution of chlorotrimethylsilane (697 μL, 2.76×2.0 mmol) was then added dropwise and stirred for 1 hour. The temperature was raised to room temperature, followed by adding water, brine, and n-hexane (50 mL). The organic layer was separated, dried over $Na_2SO_4$, filtered, and then concentrated to dryness. The residue was purified by medium pressure silica gel column chromatography (n-hexane), and desired fractions were combined and concentrated to dryness. TMS-MTPC (0.305 g, 1.08 mmol, 39%) was obtained as a colorless transparent liquid.

$^1$H-NMR (400 MHz, $CDCl_3$) δ: 0.30 (9H, s, TMS), 0.31 (9H, s, TMS), 4.06 (3H, s, $CH_3O$), 7.37 (1H, d, J=0.7 Hz, aromatic-H), 10.48 (1H, d, J=0.7 Hz, CHO).

IR (liquid film) (cm$^{-1}$): 2955, 1690 (CHO), 1512, 1323, 1250, 841.

EI-MS (m/z): 281 [M]$^+$, 266 (100%)

Synthesis of 2-methoxy-6-trimethylsilyl-4-(methylthio)pyridine-3-carbaldehyde (MeS-MTPC)

The similar procedure and post treatments as in the synthesis of Me-MTPC (instead of methyl iodide, dimethyldisulfide, 735 μL, 2.76×3.0 mmol was used) were carried out. The residue was purified by medium pressure silica gel column chromatography (after impurities were eluted by n-hexane, n-hexane:ethyl acetate=500:1), desired fractions were combined and concentrated to dryness, and MeS-MTPC (0.384 g, 1.70 mmol, 62%) was obtained as a slightly yellow solid.

$^1$H-NMR (400 MHz, CDCl$_3$) δ: 0.31 (9H, s, TMS), 2.44 (3H, s, MeS), 4.01 (3H, s, MeO), 7.03 (1H, s, aromatic-H), 10.50 (1H, s, CHO).

IR (KBr) (cm$^{-1}$): 2959, 1666 (CHO), 1555, 1504, 1339, 1246, 1038, 837.

EI-MS (m/z): 255 [M]$^+$, 240

Synthesis of 4-chloro-2-methoxy-6-(trimethylsilyl)pyridine-3-carbaldehyde(Cl-MTPC)

The similar procedure and post treatments as in the synthesis of Me-MTPC (instead of methyl iodide, hexachloroethane, 1.96 g, 2.76×3.0 mmol was used) were carried out. The residue was purified by medium pressure silica gel column chromatography (n-hexane→n-hexane:ethyl acetate=500:1→250:1), desired fractions were combined and concentrated to dryness, and Cl-MTPC (0.285 g, 1.17 mmol, 42%) was obtained as a pale yellow clear liquid.

$^1$H-NMR (400 MHz, CDCl$_3$) δ: 0.31 (9H, s, TMS), 4.08 (3H, s, MeO), 7.17 (1H, s, aromatic-H), 10.46 (1H, s, CHO).

IR (liquid film) (cm$^{-1}$): 2955, 1701 (CHO), 1562, 1531, 1339, 1250, 1034, 841.

EI-MS (m/z): 245, 243 [M]$^+$ (100%)

Synthesis of 4-bromo-2-methoxy-6-(trimethylsilyl)pyridine-3-carbaldehyde (Br-MTPC)

The similar procedure and post treatments as in the synthesis of Me-MTPC (instead of methyl iodide, carbon tetrabromide, 2.74 g, 2.76×3.0 mmol was used) were carried out. The residue was purified by medium pressure silica gel column chromatography (n-hexane:ethyl acetate=500:1), desired fractions were combined and concentrated to dryness, and Br-MTPC (0.499 g, 1.73 mmol, 63%) was obtained as a brown clear liquid.

$^1$H-NMR (400 MHz, CDCl$_3$) δ: 0.31 (9H, s, TMS), 4.07 (3H, s, MeO), 7.36 (1H, s, aromatic-H), 10.37 (1H, s, CHO).

IR (liquid film) (cm$^{-1}$): 2955, 1701 (CHO), 1558, 1524, 1339, 1250, 1026, 841.

EI-MS (m/z): 289, 287 [M]$^+$, 274, 272, 197, 182 (100%)

Synthesis of 4-iodo-2-methoxypyridine-3-carbaldehyde (DeTMS-PM)

t-Butyllithium (1.5 M in n-pentane, 6.9 mL, 9.16×1.1 mmol) was added dropwise to a dry THF (7.5 mL) solution of 2-methoxypyridine (1.00 g, 9.16 mmol) between −75° C. and −60° C. and stirred at the same temperature for 1 hour. A dry THF (10 mL) solution of FEO (1.44 g, 9.16×1.2 mmol) was added dropwise at the same temperature and stirred for 30 minutes. The temperature was raised to around −23° C., ethylene glycol dimethyl ether (DME, organic synthesis grade, 7.5 mL) was added, and subsequently n-butyllithium (1.6 M in n-hexane, 9.9 mL, 9.16×1.7 mmol) was added dropwise at between −15° C. and −25° C. and stirred at around −23° C. for 2 hours. The mixture was cooled to around −70° C., a DME (10 mL) solution of iodine (4.42 g, 9.16×1.9 mmol) was added at one-portion, and stirred at around −70° C. for 30 minutes. The temperature was raised to room temperature, 10% Na$_2$SO$_3$ (appropriate amount, until the iodine color disappeared) was added and it was stirred for 10 minutes, followed by adding water, brine, and ethyl acetate (50 mL). The organic layer was separated, dried over Na$_2$SO$_4$, filtered, and then concentrated to dryness. The residue (brown solid) was dissolved in chloroform and purified by medium pressure silica gel column chromatography (n-hexane:ethyl acetate=1000:1→100:1). Desired fractions were concentrated to dryness, and DeTMS-PM (1.31 g, 4.98 mmol, 54%) was obtained as a yellow solid.

$^1$H-NMR (400 MHz, CDCl$_3$) δ: 4.05 (3H, s, MeO), 7.54 (1H, d, J=5.4 Hz, aromatic-H), 7.85 (1H, d, J=5.4 Hz, aromatic-H), 10.21 (1H, s, CHO).

IR (KBr) (cm$^{-1}$): 2943, 1697 (CHO), 1543, 1458, 1362, 1015. EI-MS (m/z): 263 [M]$^+$ (100%)

Synthesis of 6-chloro-4-iodo-2-methoxypyridine-3-carbaldehyde (6Cl—PM)

t-Butyllithium (1.5 M in n-pentane, 5.2 mL, 6.97×1.1 mmol) was added dropwise to a dry THF (7.5 mL) solution of 6-chloro-2-methoxypyridine (1.00 g, 6.97 mmol) at between −75° C. and −60° C. and stirred at the same temperature for 1 hour. A dry THF (10 mL) solution of FEO (1.10 g, 6.97×1.2 mmol) was added dropwise at the same temperature and stirred for 30 minutes. The temperature was raised to around −23° C., ethylene glycol dimethyl ether (DME, organic synthesis grade, 7.5 mL) was added, and subsequently n-butyllithium (1.6 M in n-hexane, 7.5 mL, 6.97×1.7 mmol) was added dropwise at between −15° C. and −25° C. and stirred at around −23° C. for 2 hours. The mixture was cooled to around −70° C., and a DME (10 mL) solution of iodine (3.36 g, 6.97×1.9 mmol) was added at one-portion and stirred at around −70° C. for 30 minutes. The temperature was raised to room temperature, 10% Na$_2$SO$_3$ (appropriate amount, until the iodine color disappeared) was added and it was stirred for 10 minutes, followed by adding water, brine, and ethyl acetate (50 mL). The organic layer was separated, dried over Na$_2$SO$_4$, filtered, and then concentrated to dryness. The residue (brown solid) was dissolved in chloroform and purified by medium pressure silica gel column chromatography (n-hexane:ethyl acetate=500:1). Desired fractions were concentrated to dryness, and 6Cl—PM (1.17 g, 3.95 mmol, 57%) was obtained as a yellow solid.

$^1$H-NMR (400 MHz, CDCl$_3$) δ: 4.07 (3H, s, MeO), 7.58 (1H, d, J=0.5 Hz, aromatic-H), 10.16 (1H, d, J=0.5 Hz, CHO).

IR (KBr) (cm$^{-1}$): 2951, 1690 (CHO), 1539, 1350, 1261, 1007. EI-MS (m/z): 299, 297 [M]$^+$ (100%)

It was possible to introduce an alkyl group, a silyl group, another halogen, a sulfur atom and the like into the 4 position (R') of the pyridine ring.

In case that synthesis of other substrates known as synthetic intermediates for the CPT skeleton (R=H, R'=I, and R=Cl, R'=I) was carried out, the targets were obtained in a similar yield to that in the synthesis of compound (b).

From the above results, it has been shown that alkoxyalkylformamides [formula (I)] have the versatile ability for formylation and substitution at the ortho position to the formyl group.

Example 4

In the step of obtaining compound (d) from compound (c), the exo form (d') is formed as a by-product. For the purpose of improving the endo:exo product ratio, the reaction conditions were investigated in detail.

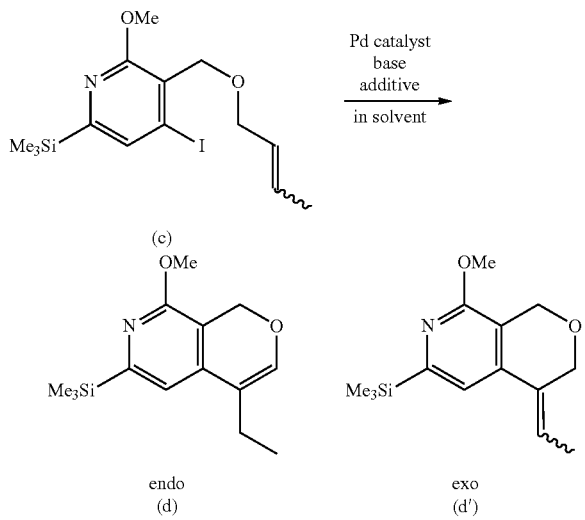

Compound (c) (0.30 g, 0.767 mmol) was dissolved in a solvent (6.1 mL) shown in Table 3, N,N-diisopropylethylamine (1.04 mL, 6.14 mmol, 8.0 eq.) and palladium acetate (17 mg, 0.077 mmol) were added at room temperature while adding or not adding tetrabutylammonium bromide (0.25 g, 0.767 mmol), and it was heated under reflux. The reaction mixture was cooled to room temperature, 10% Na$_2$SO$_3$ (4.8 mL) and n-hexane (50 mL) were added, and the organic layers (among 3 layers, upper and middle layers) were then collected. The organic layers were further washed with 1 N HCl (6.1 mL) and subsequently with water (20 mL×2), and it was then dried over anhydrous Na$_2$SO$_4$, filtered, and concentrated to dryness under reduced pressure. The residue was analyzed by HPLC, and the endo/exo ratio and the yield were determined. The yield and the endo/exo ratio are given in Table 3.

$^1$H-NMR (400 MHz, CDCl$_3$) δ: 0.26 (9H, s, TMS), 1.12 (3H, t, J=7.3 Hz, CH$_2$CH$_3$), 2.31 (2H, dq, J=1.0, 7.3 Hz, CH$_2$CH$_3$), 3.94 (3H, s, OCH$_3$), 5.00 (2H, s, OCH$_2$), 6.51 (1H, t, J=1.0 Hz, OCH=), 6.83 (1H, s, pyridine-H).

IR (liquid film) (cm$^{-1}$): 2963, 1634, 1583, 1342, 835.
EI-MS (m/z): 263 [M$^+$], 248 (100%)

Conditions for Determination of Geometric Isomer Ratio of Compound s (HPLC)
Detector: UV absorptiometer (254 nm)
Column: Inertsil ODS-2, 5 μm, 4.6 mm I.D.×250 mm
Column temperature: constant temperature at around 40° C.
Mobile phase: acetonitrile/0.01 mol/L potassium dihydrogen phosphate mixture (5:1)
Flow rate: about 1 mL/min
Area measurement range: about 50 minutes
Injection volume: 10 μL, 10 mg/10 mL (acetonitrile)
Quantitative determination method for compound d About 20 mg of a test sample was precisely weighed and dissolved in acetonitrile to accurately make 50 mL, thus giving a sample solution. About 20 mg of standard compound (d) (column purified product: known purity) was precisely weighed and dissolved in acetonitrile to accurately make 50 mL, thus giving a standard solution. 10 μL of each of the sample and the standard solution were tested by a liquid chromatographic method in accordance with a Japanese Pharmacopeia General Test Procedure under the operating conditions for determination of the geometric isomer ratio of compound (d). The peak areas of compound (d) obtained from the sample and from the standard solution were measured and the content was determined by the formula below.

Content (%) of compound (d)=At×Ws×P/(As×Wt)

At: peak area of compound d obtained from sample solution
As: peak area of compound d obtained from standard solution
Wt: sampling weight of test compound (d) (mg)
Ws: sampling weight of standard compound (d) (mg)
P: purity of standard compound (d) (%)

TABLE 3

| Run | Solvent | nBu$_4$NBr (eq.) | Reaction time (h) | endo:exo[1] | Yield[2] (%) | |
|---|---|---|---|---|---|---|
| 1 | IPE-MeCN (4:3) | 0 | 47 | 8.5:1 | 47 | (28) |
| 2 | IPE-MeCN (4:3) | 1 | 45 | 17.2:1 | 87 | |
| 3 | THF-MeCN (4:3) | 1 | 9 | 17.9:1 | 87 | |
| 4 | IPE-H$_2$O (9:1) | 1 | 72 | 9.4:1 | 27 | (53) |
| 5 | MeCN-H$_2$O (9:1) | 1 | 0.5 | 10.4:1 | 82 | |
| 6 | THF-H$_2$O (9:1) | 1 | 0.5 | 12.4:1 | 92 | |
| 7 | IPE-DMF-H$_2$O (4:3:1) | 1 | 6 | 4.3:1 | 78 | |
| 8 | DME-MeCN-H$_2$O (4:3:1) | 1 | 0.5 | 11.4:1 | 89 | |
| 9 | IPE-THF-H$_2$O (4:3:1) | 1 | 1.5 | 11.5:1 | 85 | |
| 10 | THF-MeCN-H$_2$O (4:3:1) | 1 | 0.5 | 13.8:1 | 88 | |
| 11 | ET$_2$0-MeCN-H$_2$O (4:3:1) | 1 | 1 | 18.6:1 | 85 | |
| 12 | IPE-EtCN-H$_2$O (4:3:1) | 1 | 0.5 | 17.6:1 | 88 | |

TABLE 3-continued

| Run | Solvent | nBu$_4$NBr (eq.) | Reaction time (h) | endo:exo[1] | Yield[2] (%) |
|---|---|---|---|---|---|
| 13 | CHCl$_3$-MeCN-H$_2$O (4:3:1) | 1 | 29 | 24.7:1 | 55 |
| 14 | IPE-MeCN-H$_2$O (4:3:1) | 0 | 20 | 14.9:1 | 83 |
| 15 | IPE-MeCN-H$_2$O (4:3:1) | 1 | 0.5-2 | 15.1-17.8:1 | 85-91 |

[1]Ratio obtained by correcting HPLC area using peak intensity (254 nm).
[2]Endo form, quantitatively determined by HPLC. Figure in parentheses is recovery yield of compound (c) (HPLC area %)

In case that the quaternary ammonium salt was present, the reaction was accelerated, and the product ratio was also improved (run 1 vs run 2, and run 14 vs run 15).

The presence of water was also effective in promoting the reaction (run 2 vs run 15, and run 3 vs run 10).

With regard to the organic solvent, in case that ether-type and nitrile-type solvents were combined (runs 10, 11, 12, and 15), the selectivity improved remarkably and the yield was favorable compared with cases where they were used on their own (runs 4, 5, and 6) or in other combinations (runs 7 and 9).

The chloroform-acetonitrile-water mixture gave a favorable endo:exo ratio, but other impurities were formed as by-products, and the yield was moderate.

Example 5

The solvent ratio (IPE-MeCN-water) was then examined.

The reaction conditions were the same as in Example 4. The results are given in Table 4; in case that the solvent ratio was changed, there was no great change in the endo/exo ratio. Therefore a reaction at various solvent ratios was possible.

TABLE 4

| Run | IPE-MeCN-H$_2$O Ratio | Reaction time (h) | Endo:exo[1] | Yield (%)[2] |
|---|---|---|---|---|
| 1 | 6:1:1 | 1 | 13.5:1 | 88 |
| 2 | 5:2:1 | 2 | 14.8:1 | 80 |
| 3 | 4.5:2.5:1 | 2 | 15.6:1 | 83 |
| 4 | 3.5:3.5:1 | 2 | 14.6:1 | 86 |

TABLE 4-continued

| Run | IPE-MeCN-H$_2$O Ratio | Reaction time (h) | Endo:exo[1] | Yield (%)[2] |
|---|---|---|---|---|
| 5 | 3:4:1 | 0.5 | 15.1:1 | 90 |
| 6 | 1:6:1 | 0.5 | 14.6:1 | 81 |

[1]Ratio obtained by correcting HPLC area using peak intensity (254 nm).
[2]Endo form, quantitatively determined by HPLC.

Example 6

An experiment was next carried out by changing the solvent, catalyst, and base.

Compound (c) (0.30 g, 0.767 mmol) was dissolved in a solvent (6.1 mL) shown in Table 5, tetrabutylammonium bromide (0.25 g, 0.767 mmol), a base (6.14 mmol), and a catalyst (0.077 mmol) were added at room temperature, and it was heated under reflux. The reaction mixture was cooled to room temperature and filtered, 10% Na$_2$SO$_3$ (4.8 mL) and n-hexane (50 mL) were added to the solution, and the organic layers (among 3 layers, upper and middle layers) were then collected. The organic layers were further washed with 1 N HCl (6.1 mL) and subsequently with water (20 mL×2), and it was then dried over anhydrous Na$_2$SO$_4$, filtered, and concentrated to dryness under reduced pressure. The residue was analyzed by HPLC, and the endo/exo ratio and yield were determined. The results are given in Table 5. In case that the solvent was an acetonitrile-water mixture, the catalyst was palladium (II) chloride, and the base was triethylamine, gave very favorable results (run 8) for both the yield (93%) and the endo/exo ratio (29.8:1). The endo/exo ratio was corrected by the HPLC peak intensity ratio (254 nm).

TABLE 5

| Run | Solvent | Catalyst 10 mol % | Base 8 eq. | Time h | Yield % | endo:exo[e] |
|---|---|---|---|---|---|---|
| 1 | MeCN | Pd(OAc)$_2$ | i-Pr$_2$NEt | 3 | 79 | 10.9:1.0 |
| 2 | MeCN—H$_2$O[a] | " | " | 1 | 82 | 10.4:1.0 |
| 3 | IPE-H$_2$O[a] | " | " | 72 | 27 | 9.4:1.0 |
| 4 | IPE-MeCN[b] | " | " | 45 | 87 | 17.2:1.0 |
| 5 | IPE-MeCN—H$_2$O[c] | " | " | 1 | 90 | 17.8:1.0 |
| 6 | " | " | Et$_3$N | 1 | 87 | 19.2:1.0 |
| 7 | " | PdCl$_2$ | " | 1 | 95 | 26.4:1.0 |
| 8 | MeCN—H$_2$O[d] | " | " | 1 | 93 | 29.8:1.0 |
| Ref. Ex. | DMF | Pd(OAc)$_2$ | K$_2$CO$_3$[f] | 1 | 69 | 4.3:1.0 | temp.) reflux
[a]9:1
[b]4:3
[c]4:3:1
[d]7:1
[e]HPLC (corrected by peak intensity ratio)
[f]4 eq.

Example 7

An experiment was next carried out by changing the catalyst and the base.

Compound (c) (0.30 g, 0.767 mmol) was dissolved in a diisopropyl ether-acetonitrile-water mixture (4:3:1, 6.1 mL), tetrabutylammonium bromide (0.25 g, 0.767 mmol), triethylamine (0.85 mL, 6.14 mmol, 8 eq.) or potassium carbonate (0.212 g, 1.53 mmol, 4 eq), and a catalyst shown in Table 5 (0.077 mmol) were added at room temperature, and it was heated under reflux. The reaction mixture was cooled to room temperature and filtered, 10% $Na_2SO_3$ (4.8 mL) and n-hexane (50 mL) were added, and the organic layers (among 3 layers, upper and middle layers) were then collected. The organic layers were further washed with 1 N HCl (6.1 mL) and subsequently water (20 mL×2), dried with anhydrous $Na_2SO_4$, filtered, and concentrated to dryness under reduced pressure. The residue was analyzed by HPLC, and the endo/exo ratio and yield were determined. The results are given in Table 6.

TABLE 6

| Run | Catalyst | Base | Reaction time (h) | endo:exo[1] | Yield (%)[2] |
|---|---|---|---|---|---|
| 1 | $Pd(OAc)_2$ | $Et_3N$ | 1 | 19.2:1 | 87 |
| 2 | $Pd(OAc)_2$ | $K_2CO_3$ | 40 | 10.2:1 | 47 (33) |
| 3 | $(Ph_3P)_4Pd$ | $Et_3N$ | 119 | 1:11.1 | — (41) |
| 4 | $(Ph_3P)_2PdCl_2$ | $Et_3N$ | 0.5 | 1:2.1 | 40 |
| 5 | $PdCl_2$ | $Et_3N$ | 0.5 | 26.4:1 | 95 |
| 6 | $(MeCN)_2PdCl_2$ | $Et_3N$ | 1 | 25.8:1 | 95 |
| 7 | $(PhCN)_2PdCl_2$ | $Et_3N$ | 1 | 27.0:1 | 93 |
| 8 | $(dba)_2Pd$ | $Et_3N$ | 5 | 25.6:1 | 87 |
| 9 | $[(allyl)PdCl]_2$ | $Et_3N$ | 91 | 18.5:1 | 50 (36) |
| 10 | $(dppf)PdCl_2$ | $Et_3N$ | 1 | 1:1.3 | 50 |
| 11 | 20%$Pd(OH)_2$—C | $Et_3N$ | 70 | 16.9:1 | 88 |
| 12 | 10%Pd—C | $Et_3N$ | 15 | 16.9:1 | 79 |

[1]Ratio obtained by correcting HPLC area using peak intensity (254 nm).
[2]Endo form, figure in parentheses is recovery yield of compound (c) (HPLC area %)

The use of triethylamine as the base improved the endo:exo ratio (run 15 in Table 3 vs run 1 in Table 6). The catalysts of runs 5 to 8 further improved the selectivity, and compound (d) was obtained in good yield.

As described above, by use of an ether-type-water mixture or an ether-type-nitrile-type-water mixture as the solvent, triethylamine as the base, and palladium (II) chloride, palladium (II) acetate, palladium-carbon, palladium hydroxide-carbon, bis(acetonitrile)palladium (II) chloride, bis(benzonitrile)palladium (II) chloride, or bis(dibenzylideneacetone) palladium (0) as the catalyst in the presence of a quaternary ammonium salt, compound (d) is obtained with a better endo: exo ratio and yield than a reference example in [Table 5] under known literature conditions.

Reference Example

It has been reported that the use of a Wilkinson complex in an intramolecular Heck reaction of a compound (C) analog improves the endo:exo ratio (Bankston, D.; Fang, F.; Huie, E.; Xie, S., J. Org. Chem. 1999, 64, 3461-3466). Although the reported conditions were applied to compound (C) (run 1) and reaction conditions such as the amount of Wilkinson complex added were examined, no improvement in the endo/exo ratio or the yield was observed.

TABLE 7

| Run | Solvent[1] | Catalyst[2] mol % | Additive[3] mol % | Base mol times | $nBu_4NX$ X(mol times) | Temp.[4] (° C.) | Time h | endo:exo[5] | Yield[6] % |
|---|---|---|---|---|---|---|---|---|---|
| 1-1 | DMF | 2.3 | A (0.8) | $K_2CO_3$(2) | Cl(0.5) | 21→85 | 47 | 7.2:1 | 63 |
| 1-2 | DMF | 2.3 | A (0.8) | $K_2CO_3$(2) | Cl(0.5) | 24→90 | 21 | 8.1:1 | 55 |
| 3 | I-M-H | 10 | A (3.3) | $K_2CO_3$(2) | Br(1) | 24→90 | 1.5 | 4.8:1 | 69 |
| 4 | I-M-H | 10 | A (3.3) | $iPr_2NEt$(8) | Br(1) | 21→reflux | 1 | 1:1.1 | 55 |

[1]I-M-H = IPE-MeCN-water(4:3:1)
[2]$Pd(OAc)_2$
[3]A = $(Ph_3P)_3RhCl$, B = $RhCl_3H_2O$
[4](Temp reagent added)→(Reaction temp)
[5]Ratio obtained by correcting HPLC area using peak intensity (254 nm)
[6]Endo form Processes for preparation and analytical methods of the compounds used in the Examples above are illustrated below.

Synthesis of N-ethoxyethyl-N-methylbenzylamine (BnEO)

Process 1) NaH (washed with hexane in advance, 8.78 g, 0.305×1.2 mol) was added to a dry THF (300 mL) solution of N-methylbenzylamine (39 mL, 0.305 mol) under an argon atmosphere at room temperature. After stirring at room temperature for 30 minutes, a dry THF (100 mL) solution of bromoethyl ethyl ether (51 mL, 0.305×1.5 mol) was added dropwise, and further heated under reflux under an argon atmosphere for 24 hours. After cooling to room temperature, water (350 mL) was carefully added for dissolution of insoluble materials, followed by adding ethyl acetate (350 mL). The organic layer was separated, further washed with brine (200 mL) and then concentrated to dryness. Since insoluble materials precipitated in the residual fraction, they were filtered off and washed with ethyl acetate, and the filtrate was again concentrated to dryness. The residue was purified by vacuum distillation (fraction at 1.0 to 1.1 kpa and 95° C. to 110° C. collected), and BnEO (49.73 g, 0.257 mol, 84%) was obtained as a colorless transparent liquid.

$^1$H-NMR (400 MHz, $CDCl_3$) δ: 1.21 (3H, t, J=7.1 Hz, $CH_3$), 2.27 (3H, s, $CH_3$), 2.62 (2H, t, J=6.1 Hz, $CH_2$), 3.49 (2H, quar., J=7.1 Hz, $CH_2$), 3.57 (2H, s, $CH_2$), 3.57 (2H, t, J=6.1 Hz, $CH_2$), 7.22 to 7.34 (5H, m, aromatic-H).

IR (liquid film) ($cm^{-1}$): 3028, 2866, 1454, 1111 (ether), 737 (monosubstituted benzene), 698 (monosubstituted benzene).

EI-MS (m/z): 193 $[M]^+$, 134 (100%)

Process 2) Bromoethyl ethyl ether (1.3 mL, 7.76×1.3 mmol) was added to a methanol (5 mL) solution of N-methylbenzylamine (1.0 mL, 7.76 mmol) at room temperature, and heated under reflux for 18 hours. After cooling to room temperature, the residue obtained by concentration to dryness was mixed with water and saturated NaHCO$_3$ to make it basic (pH paper), and extracted with chloroform (2 times). The combined organic layers were dried over anhydrous Na$_2$SO$_4$, filtered, and subsequently concentrated to dryness. The residue was purified by medium pressure silica gel column chromatography (n-hexane:ethyl acetate=4:1), a target fraction was concentrated to dryness, and BnEO (0.907 g, 4.69 mmol, 61%) was obtained as a pale yellow clear liquid.

Synthesis of N-ethoxyethyl-N-methylformamide
(FEO)

10% Pd—C (manufactured by Kawaken Fine Chemicals, Co. Ltd., M, Dry, moisture content 1.7%, 2.24 g) and formic acid (43 mL, 0.223×5 mol) were added to a methanol (430 mL) solution of BnEO (43.11 g, 0.223 mol) under an argon atmosphere and it was heated under reflux for 90 minutes. After cooling to room temperature, the Pd—C was removed by filtration with a pad of Celite, washed with methanol, and the filtrate was concentrated to dryness. Toluene (430 mL) was added to the residue and heated under reflux for 20 hours while removing water formed as a by-product with a Dean-Stark tube. After cooling to room temperature, K$_2$CO$_3$ (90 g, 0.223×3 mol) was added and it was stirred at room temperature for 3 hours. Insoluble materials were removed by filtration, washed with toluene, and the filtrate was then concentrated to dryness. The residue was purified by vacuum distillation with a Vigreux fractionating column (15 cm) (fraction at 0.5 to 0.7 kpa, 78° C. to 80° C. collected), and FEO (24.36 g, 0.186 mol, 83%) was obtained as a colorless transparent liquid.

$^1$H-NMR (400 MHz, CDCl$_3$) δ: 1.18, 1.19 (3H, each t, each J=7.1 Hz, CH$_3$), 2.92, 3.04 (3H, each s, CH$_3$), 3.36 to 3.57 (6H, m, CH$_{2×3}$), 8.06 (1H, s, CHO).
IR (liquid film) (cm$^{-1}$): 2974, 2866, 1678 (CHO), 1396, 1119 (ether).
EI-MS (m/z): 131-[M$^+$], 85, 72 (100%).

Synthesis of N-methoxyethyl-N-methylbenzylamine
(BnMO)

The synthesis of BnMO was carried out in a manner similar to that of BnEO (process 2) using N-methylbenzylamine (15 mL, 0.116 mol), bromoethyl methyl ether (12 mL, 0.116×1.1 mmol), and ethanol (200 mL) as a solvent. BnMO (12.09 g, 67.46 mmol, yield 58%) was obtained as a pale yellow clear liquid.
[Purification was Carried Out by Medium Pressure Silica Gel Column (Ethyl Acetate).]
$^1$H-NMR (400 MHz, CDCl$_3$) δ: 2.27 (3H, s, CH$_3$), 2.61 (2H, t, J=5.9 Hz, CH$_2$), 3.34 (3H, s, CH$_3$), 3.52 (2H, t, J=5.9 Hz, CH$_2$), 3.56 (2H, s, CH$_2$), 7.22 to 7.33 (5H, m, aromatic-H).
IR (liquid film) (cm$^{-1}$): 3028, 2874, 1454, 1119 (ether), 737 (monosubstituted benzene), 698 (monosubstituted benzene).
EI-MS (m/z):179-[M]$^+$, 134, 91 (100%)

Synthesis of N-methoxyethyl-N-methylformamide
(FMO)

The synthesis of FMO was carried out in a manner similar to that of FEO using BnMO (10.00 g, 55.79 mmol). FMO (3.60 g, 30.70 mmol, yield 55%) was obtained as a colorless transparent liquid. (In a purification by vacuum distillation, a fraction at 4.2 kpa, 47° C. to 54° C. was collected.)
$^1$H-NMR (400 MHz, CDCl$_3$) δ: 2.86, 2.98 (3H, each s, CH$_3$), 3.00, 3.00 (3H, each s, CH$_3$), 3.34 to 3.52 (4H, m, CH$_2$CH$_2$), 8.00, 8.01 (1H, each s, CHO).
IR (liquid film) (cm$^{-1}$): 2928, 2878, 1674 (CHO), 1396, 1119 (ether).
EI-MS (m/z): 117-[M]$^+$, 85, 72 (100%)

Synthesis of N-ethyl-N-methoxyethylbenzylamine
(BnEA)

The synthesis of BnEA was carried out in a manner similar to that of BnEO (process 2) using N-ethylbenzylamine (15 mL, 0.101 mol), bromoethyl methyl ether (0.101×1.2 mol), and ethanol (100 mL) as a solvent. BnEA (9.17 g, 47.46 mmol, yield 47%) was obtained as a yellow-orange clear liquid.
[Purification was carried out by medium pressure silica gel column chromatography (n-hexane:ethyl acetate=3:2).]
$^1$H-NMR (400 MHz, CDCl$_3$) δ: 1.07 (3H, t, J=7.1 Hz, CH$_3$), 2.59 (2H, guar., J=7.1 Hz, CH$_2$), 2.68 (2H, t, J=6.3 Hz, CH$_2$), 3.33 (3H, s, CH$_3$), 3.48 (2H, t, J=6.3 Hz, CH$_2$), 3.65 (2H, s, CH$_2$), 7.22 to 7.38 (5H, m, aromatic-H).
IR (liquid film) (cm$^{-1}$): 3028, 2970, 2812, 1454, 1123 (ether), 733 (monosubstituted benzene), 698 (monosubstituted benzene).
EI-MS (m/z): 193 [M]$^+$, 148 (100%)

Synthesis of N-ethyl-N-methoxyethylformamide
(FEA)

The synthesis of FEA was carried out in a manner similar to that of FEO using BnEA (5.57 g, 28.82 mmol). FEA (2.45 g, 18.66 mmol, yield 65%) was obtained as a colorless transparent liquid. (In a purification by vacuum distillation, a fraction at 0.9 to 1.0 kpa, 85° C. to 86° C. was collected.)
$^1$H-NMR (400 MHz, CDCl$_3$) δ: 1.14, 1.19 (3H, each t, each J=7.1 Hz, CH$_3$), 3.34, 3.35 (3H, each s, CH$_3$), 3.37 to 3.55 (6H, m, CH$_{2×3}$), 8.03, 8.10 (5H, m, aromatic-H).
IR (liquid film) (cm$^{-1}$): 2936, 2878, 1670 (CHO), 1431, 1119 (ether).
EI-MS (m/z): 131-[M]$^+$, 99, 86 (100%)

Synthesis of N-ethoxyethyl-N-ethylbenzylamine
(BnEE)

The synthesis of FEA was carried out in a manner similar to that of BnEO (process 2) using N-ethylbenzylamine (15 mL, 0.101 mol), bromoethyl ethyl ether (17 mL, 0.101×1.5 mol), and ethanol (100 mL) as a solvent. BnEE (12.79 g, 61.69 mmol, yield 61%) was obtained as a pale yellow clear liquid.
[Purification was carried out by medium pressure silica gel column chromatography (ethyl acetate:n-hexane=4:1).]
$^1$H-NMR (400 MHz, CDCl$_3$) δ: 1.08 (3H, t, J=7.1 Hz, CH$_3$), 1.21 (3H, t, J=7.1 Hz, CH$_3$), 2.61 (2H, quar., J=7.1 Hz, CH$_2$), 2.71 (2H, t, J=6.6 Hz, CH$_2$), 3.49 (2H, quar., J=7.1 Hz, CH$_2$), 3.54 (2H, t, J=6.6 Hz, CH$_2$), 3.67 (2H, s, CH$_2$), 7.24 to 7.38 (5H, m, aromatic-H).
IR (liquid film) (cm$^{-1}$): 3028, 2970, 1454, 1115 (ether), 733 (monosubstituted benzene), 698 (monosubstituted benzene).
EI-MS (m/z): 207-[M]$^+$, 148 (100%)

Synthesis of N-ethoxyethyl-N-ethylformamide (FEE)

The synthesis of FEE was carried out in a manner similar to that of FEO using BnEE (10.00 g, 48.23 mmol). FEE (4.80 g, 33.03 mmol, yield 68%) was obtained as a colorless transparent liquid. (In a purification by vacuum distillation, a fraction at 0.8 to 0.9 kpa, 91° C. to 92° C. was collected.)

$^1$H-NMR (400 MHz, CDCl$_3$) δ: 1.13, 1.17, 1.17, 1.19 (6H, each t, J=7.1 Hz, CH$_{3\times2}$), 3.34 to 3.56 (8H, m, CH$_{2\times4}$), 8.03, 8.09 (1H, each s, CHO).

IR (liquid film) (cm$^{-1}$): 2974, 2870, 1674 (CHO), 1431, 1119 (ether).

EI-MS (m/z): 145 [M]$^+$, 99, 86 (100%)

Synthesis of N-methoxymethyl-N-methylformamide (FMM)

NaH (washed with n-hexane in advance, 6.71 g, 0.254×1.1 mol) was added to a dry THF (150 mL) solution of N-methylformamide (15.00 g, 0.254 mol) under an argon atmosphere with ice-bath cooling, and stirred for 30 minutes. A dry THF (20 mL) solution of chloromethyl methyl ether (24.54 g, 0.254×1.2 mol) was added dropwise under an argon atmosphere at the same temperature and then stirred for 2 hours, and further stirred at room temperature for 3 hours. After cooling with ice-bath, n-hexane (100 mL) was added to the reaction mixture and it was stirred for 1 hour, and insoluble materials were then removed by filtration with a pad of Celite. A residue obtained by concentrating the filtrate to dryness (40° C., 15 mmHg) was purified by vacuum distillation (fraction at 1.6 kpa, 66° C. to 68° C. collected), and FMM (7.90 g, 76.61 mmol, 30%) was obtained as a colorless transparent liquid.

$^1$H-NMR (400 MHz, CDCl$_3$) δ: 2.92, 2.98 (3H, each s, CH$_3$), 3.25, 3.29 (3H, each s, CH$_3$), 4.63, 4.77 (2H, each s, CH$_2$), 8.19 (1H, s, CHO).

IR (liquid film) (cm$^{-1}$): 2936, 1674 (CHO), 1400, 1099 (ether). EI-MS (m/z): 103 [M]$^+$, 88 (100%)

Synthesis of N-ethoxypropyl-N-methylformamide (FEP)

Formic acid (9.4 mL, 0.208×1.2 mol) was added to a toluene (250 mL) solution of 3-ethoxypropylamine (25 mL, 0.208 mol) at room temperature, and heated under reflux for 17 hours while removing water formed as a by-product with a Dean-Stark tube. After cooling to room temperature, K$_2$CO$_3$ (14 g, 0.208×0.5 mol) was added and it was stirred for 90 minutes. Insoluble materials were removed by filtration, washed with toluene, and the filtrate was concentrated to dryness. The residue was purified by vacuum distillation with a Vigreux fractionating column (15 cm) (fraction at 0.6 kpa, 114° C. to 115° C. collected), and N-(3-ethoxypropyl)formamide (21.79 g, 0.166 mol, 80%) was obtained as a colorless transparent liquid.

NaH (washed with n-hexane in advance, 2.01 g, 76.24×1.1 mmol) was added to a dry THF (100 mL) solution of N-(3-ethoxypropyl)formamide (10.00 g, 76.24 mmol) under an argon atmosphere with ice-bath cooling, and stirred for 30 minutes. A dry THF (10 mL) solution of methyl iodide (5.7 mL, 76.24×1.2 mmol) was added dropwise to the reaction mixture under an argon atmosphere with ice-bath cooling, it was then stirred for 30 minutes, and further stirred at room temperature for 90 minutes. NaH (washed with n-hexane in advance, 0.20 g, 76.24×0.1 mmol) was again added and it was stirred at room temperature for 1 hour. After cooling with ice-bath, n-hexane (100 mL) was added to the reaction mixture and it was stirred for 1 hour, and insoluble materials were then removed by filtration with a pad of Celite. A residue obtained by concentrating the filtrate to dryness was purified by vacuum distillation (fraction at 0.6 kpa, 91° C. collected), and FEP (4.17 g, 28.68 mmol, 38%) was obtained as a pale yellow clear liquid.

$^1$H-NMR (400 MHz, CDCl$_3$) δ: 1.19, 1.20 (3H, each t, each J=7.1 Hz, CH$_3$), 1.78 to 2.30 (2H, m, CH$_2$), 2.86, 2.96 (3H, each s, CH$_3$), 3.45 to 3.50 (6H, m, CH$_2$×3), 8.03, 8.09 (1H, each s, CHO).

IR (liquid film) (cm$^{-1}$): 2932, 2862, 1678 (CHO), 1397, 1111 (ether).

EI-MS (m/z): 145 [M]$^+$, 116, 101, 72 (100%)

INDUSTRIAL APPLICABILITY

By use of the synthetic process of the present invention, highly pure tricyclic ketones can be synthesized in a short period of time, and by use of these intermediates, a total synthesis of CPT analogs can be accomplished efficiently and practically.

The invention claimed is:

1. An alkoxyalkylformamide represented by formula (I)

(wherein R and R' are independently alkyl having 1 or 2 carbons and n is an integer of 2 to 3, but excluding one in which n is 2 and R and R' are both ethyl).

2. A process for preparing a tricyclic ketone (k), represented by the formula below, for synthesizing camptothecin analogs

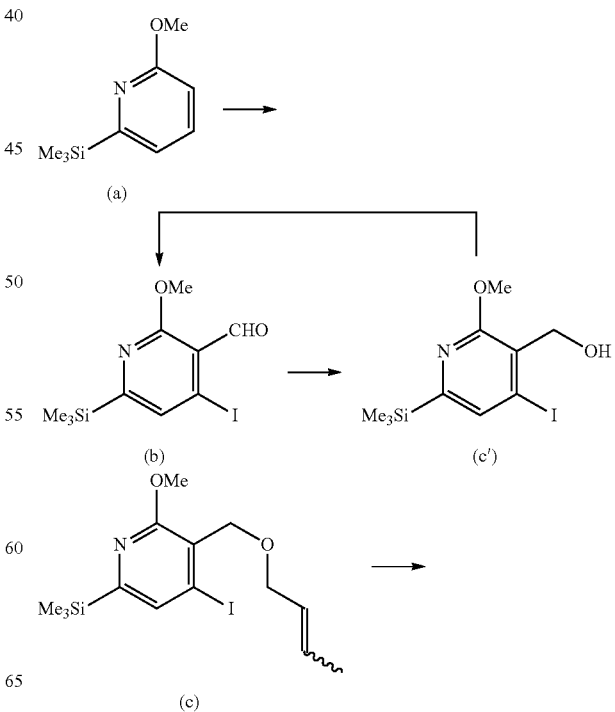

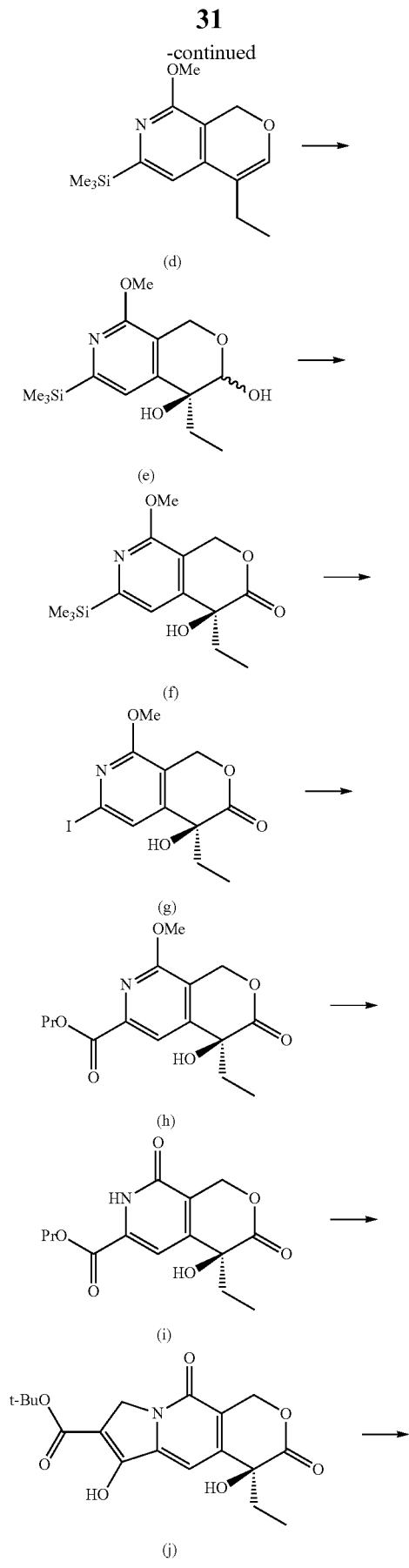

(d)
(e)
(f)
(g)
(h)
(i)
(j)

-continued

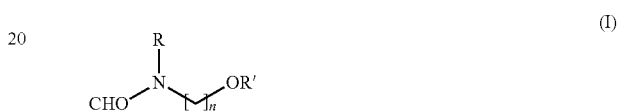

(k)

(wherein Me denotes a methyl group, Pr denotes a propyl group, and t-Bu denotes a t-butyl group), the process comprising a step (1) of mixing the above compound (a), the alkoxyalkylformamide represented by formula (I)

$$\underset{CHO}{\overset{R}{\underset{|}{N}}}\underset{n}{\overset{}{\diagdown}}OR'$$ (I)

(wherein R and R' are independently alkyl having 1 or 2 carbons and n is an integer of 1 to 3, but excluding one in which n is 1 and R and R' are both methyl, one in which n is 1, R is methyl and R' is ethyl and one in which n is 2 and R and R' are both ethyl), and a lithiation reagent, and subsequently mixing with an iodination reagent to give compound (b).

3. The process for preparing the tricyclic ketone (k) according to claim 2, further comprising a step (2) of mixing and stirring in a solvent at least one type of palladium catalyst selected from palladium (II) chloride, palladium (II) acetate, palladium-carbon, palladium hydroxide-carbon, bis(acetonitrile)palladium (II) dichloride, bis(benzonitrile)palladium (II) dichloride, and bis(dibenzylideneacetone)palladium (0), compound (c), a base, and a quaternary ammonium salt to give compound (d).

4. The process for preparing the tricyclic ketone (k) according to claim 2, wherein in step (1) the compound represented by formula (I) in which n is 2 is used.

5. The process for preparing the tricyclic ketone (k) according to claim 2, wherein in step (1) the lithiation reagent is n-butyllithium.

6. The process for preparing the tricyclic ketone (k) according to claim 3, wherein in step (2) the solvent is a water-containing solvent.

7. The process for preparing the tricyclic ketone (k) according to claim 3, wherein in step (2) the solvent is a mixture of a nitrile-type organic solvent and water.

8. The process for preparing the tricyclic ketone (k) according to claim 3, wherein in step (2) the solvent is a mixture of an ether-type organic solvent, a nitrile-type organic solvent, and water.

9. A method for preparation of camptothecin analogs comprising obtaining the tricyclic ketone (k) according to claim 2.

10. A process for synthesizing camptothecin analogs, the process comprising obtaining the tricyclic ketone (k) according to claim 2 and reacting the tricyclic ketone (k) with 2'-amino-5'-hydroxypropiophenone.

11. The process for preparing the tricyclic ketone (k) according to claim 3, wherein in step (1) the compound represented by formula (I) in which n is 2 is used.

12. The process for preparing the tricyclic ketone (k) according to claim 3, wherein in step (1) the lithiation reagent is n-butyllithium.

13. The process for preparing the tricyclic ketone (k) according to claim 4, wherein in step (1) the lithiation reagent is n-butyllithium.

14. A method for preparation of camptothecin analogs comprising obtaining the tricyclic ketone (k) according to claim 3.

15. A process for synthesizing camptothecin analogs, the process comprising obtaining the tricyclic ketone (k) according to claim 3 and reacting the tricyclic ketone (k) with 2'-amino-5'-hydroxypropiophenone.

* * * * *

UNITED STATES PATENT AND TRADEMARK OFFICE
CERTIFICATE OF CORRECTION

PATENT NO. : 8,466,287 B2
APPLICATION NO. : 13/278579
DATED : June 18, 2013
INVENTOR(S) : Hiroyuki Nishiyama et al.

Page 1 of 1

It is certified that error appears in the above-identified patent and that said Letters Patent is hereby corrected as shown below:

Title Page, Item (62) should read:

Related U.S. Application Data

(62)  Division of application No. 11/921,776, filed as application No. PCT/JP2006/311482 on Jun. 8, 2006, now Pat. No. 8,067,595.

Signed and Sealed this
Twenty-fourth Day of September, 2013

Teresa Stanek Rea
*Deputy Director of the United States Patent and Trademark Office*